(12) United States Patent
Vogtel et al.

(10) Patent No.: US 6,504,040 B1
(45) Date of Patent: Jan. 7, 2003

(54) INTEGRATED METHOD FOR PRODUCING EPOXIDES FROM OLEFINS

(75) Inventors: Peter Vogtel, Leverkusen (DE);
Ernst-Ulrich Dorf, Krefeld (DE);
Gerhard Wegener, Mettmann (DE);
Markus Weisbeck, Köln-Holweide (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/857,674

(22) PCT Filed: Dec. 1, 1999

(86) PCT No.: PCT/EP99/09340

§ 371 (c)(1),
(2), (4) Date: Jun. 7, 2001

(87) PCT Pub. No.: WO00/35894

PCT Pub. Date: Jun. 22, 2000

(30) Foreign Application Priority Data

Dec. 11, 1998 (DE) .......................................... 198 57 137

(51) Int. Cl.⁷ ...................... C07D 301/14; C07D 301/12
(52) U.S. Cl. ...................... 549/525; 549/526; 549/531
(58) Field of Search ................................ 549/525, 526, 549/531

(56) References Cited

U.S. PATENT DOCUMENTS

| | | | |
|---|---|---|---|
| 4,009,252 A | 2/1977 | Izumi et al. | 423/584 |
| 4,279,883 A | 7/1981 | Izumi et al. | 423/584 |
| 4,336,238 A | 6/1982 | Dalton, Jr. et al. | 423/584 |
| 4,336,239 A | 6/1982 | Dalton, Jr. et al. | 423/584 |
| 4,410,501 A | 10/1983 | Taramasso et al. | 423/326 |
| 4,661,337 A | 4/1987 | Brill | 423/584 |
| 4,833,260 A | 5/1989 | Neri et al. | 549/531 |
| 4,954,653 A | 9/1990 | Bellussi et al. | 564/223 |
| 5,221,795 A | 6/1993 | Clerici et al. | 549/531 |
| 5,352,645 A | 10/1994 | Schwartz | 502/262 |
| 5,523,426 A | 6/1996 | Jubin, Jr. et al. | 549/531 |
| 5,599,955 A | 2/1997 | Vora et al. | 549/525 |
| 5,599,956 A | 2/1997 | Pujado et al. | 549/531 |
| 5,623,090 A | 4/1997 | Haruta et al. | 568/360 |
| 6,008,389 A | 12/1999 | Grosch et al. | 549/533 |

FOREIGN PATENT DOCUMENTS

| | | |
|---|---|---|
| DE | 196 23 608 | 12/1997 |
| DE | 196 23 611 | 12/1997 |
| DE | 196 42 770 | 4/1998 |
| DE | 19 723 950 | 12/1998 |
| EP | 0 117 306 | 8/1988 |
| EP | 0 230 949 | 7/1992 |
| EP | 0 812 836 | 12/1997 |
| WO | 92/04976 | 4/1992 |
| WO | 96/23023 | 8/1996 |
| WO | 98/00413 | 1/1998 |
| WO | 98/00415 | 1/1998 |

*Primary Examiner*—Amelia Owens
(74) *Attorney, Agent, or Firm*—Joseph C. Gil; Lyndanne M. Whalen

(57) ABSTRACT

The invention relates to an integrated process for the preparation of epoxidised olefins. In the first stage, dilute hydrogen peroxide solutions are prepared from the elements hydrogen and oxygen and are reacted in a subsequent liquid-phase epoxidation with olefin in the presence of titanium silicalite to form epoxidised olefins, and the solvents are returned to the $H_2O_2$ process again.

11 Claims, 1 Drawing Sheet

INTEGRATED METHOD FOR PRODUCING EPOXIDES FROM OLEFINS

The invention relates to an integrated process for the preparation of epoxidised olefins. In the first stage, dilute hydrogen peroxide solutions are prepared from the elements hydrogen and oxygen, with catalysis, and are reacted in a subsequent liquid-phase epoxidation with olefin in the presence of titanium silicalite to form epoxidised olefin, and the solvents are returned to the $H_2O_2$ process again.

Propene oxide is one of the most important basic chemicals in the chemical industry. Its field of application, where over 60% is used, is the plastics sector, especially in the preparation of polyether polyols for the synthesis of polyurethanes. In addition, the propene oxide derivatives also make up relatively large shares of the market in the field of the glycols, especially lubricants and antifreeze.

The preparation of epoxidised olefins is known in principle. An olefin is used as the starting material and is oxidised by a very wide variety of methods. For ecological reasons, however, oxidation using hydrogen peroxide or air is to be preferred.

Titanium silicalite-catalysed epoxidation using pure oxygen as the oxidising agent is possible in the presence of a redox system consisting of alkylanthrahydroquinone and alkylanthraquinone (U.S. Pat. No. 5,221,795). A disadvantage of this reaction is the continuous loss of small amounts of anthraquinone and organic solvents as a result of oxidative decomposition of those organic compounds.

Using titanium silicalites containing platinum metal, propene oxidation is possible with a low yield (approximately from 1 to 2%) and with unsatisfactory propene oxide selectivities of from 60 to 70% using a gas mixture consisting of molecular oxygen and molecular hydrogen (WO-97/47 386, WO-96/023 023). Hydrogenations occurring as a side reaction lead to large amounts of propane as a secondary product. U.S. Pat. No. 5,623,090 and WO-98/00 413-15 disclose a direct oxidation of propene to propene oxide using molecular oxygen in the presence of hydrogen. Commercially available titanium dioxide containing finely dispersed gold particles is used as the catalyst. In addition to low yields, all those processes have the disadvantage that they are very expensive owing to the gold content of the catalyst. For economical use, therefore, the development of catalysts having markedly better catalyst activities with a greatly increased useful life of the catalyst continues to be absolutely necessary.

U.S. Pat. No. 4,833,260 describes titanium silicalite catalysts which effectively permit the epoxidation of olefins using the oxidising agent hydrogen peroxide in the liquid phase. In the case of the silicalites, a small portion of the lattice silicon has been replaced by titanium (U.S. Pat. No. 4,410,501). However, the high costs of hydrogen peroxide as an oxidising agent have hitherto prevented its use on a large scale. A large part of the costs involved in the use of hydrogen peroxide arise due to the hydrogen peroxide itself, since the concentrations of hydrogen and oxygen during the preparation must be observed very closely for safety reasons. Reaction solutions containing low concentrations of $H_2O_2$ are predominantly obtained, and they must then be concentrated, purified and stabilised in costly operations.

The preparation of hydrogen peroxide is in principle state of the art.

It has for a long time been known that hydrogen peroxide can also be prepared directly from the elements hydrogen and oxygen using suitable catalysts.

It has also for a long time been known that mixtures of gaseous oxygen and hydrogen yield explosive gas mixtures. For that reason, all industrial $H_2O_2$ processes are carried out using an indirect combination of hydrogen and oxygen.

Over 90% of world hydrogen peroxide production is currently carried out by the anthraquinone process, in which alkylanthraquinones are typically used as the chemical auxiliary substances. The disadvantage of this reaction is the continuous loss of small amounts of anthraquinone and organic solvents as a result of the oxidation and of thermal decomposition of those organic compounds and cost-intensive extraction, purification and distillation steps.

The direct synthesis of $H_2O_2$ from the elements hydrogen and oxygen is the subject of intensive research efforts, but as yet has not led to any commercial application. Aside from the safety problems, the most important problem is to prevent the hydrogen peroxide that is formed from subsequently decomposing to water and oxygen. That problem is solved by means of continuous processes which operate at high rates of flow. The result is, however, that at low reaction rates, the hydrogen peroxide concentrations contained in the discharge are too low for economical use of that process.

For the formation of hydrogen peroxide from hydrogen and oxygen using palladium-containing catalysts, U.S. Pat. No. 4,009,252 discloses an optimum ratio of $O_2$ to $H_2$ in the range of from 1.5:1 to 20:1, i.e. in the explosive range.

The transition metals of sub-group 8, mostly palladium or platinum, are most frequently used as the catalytically active species. The noble metal can be applied to various supports, such as $TiO_2$, $SiO_2$, $Al_2O_3$, Teflon, activated carbon or catalyst monoliths produced from woven fabrics, such as, for example, V4a, with activated carbon being most frequently used. Processes based on such catalyst systems have been patented by numerous firms and institutions, such as, for example, U.S. Pat. Nos. 4,279,883, 4,661,337, EP-117 306 and DE-196 42 770.

U.S. Pat. Nos. 4,336,238 and 4,336,239 describe the reaction of hydrogen and oxygen to form hydrogen peroxide using palladium-containing catalysts in organic solvents or solvent mixtures, which optionally also contain water. The hydrogen peroxide concentrations of at most 2.4 wt. % which are obtained using reaction gas mixtures containing less than 5 vol. % hydrogen are too low for economical use. Moreover, after an operating time of 285 hours, the catalyst activity has fallen to 69% of the original value, which is still too low for industrial use.

U.S. Pat. No. 5,352,645 and WO-92/04 976 describe special solid supports of spray-dried coloidal silica gel. EP-627 381 discloses the use of niobium, tantalum, molybdenum or tungsten oxides as support materials which are distinguished by high resistance to acid.

In the mentioned specifications, however, the hydrogen peroxide is always prepared by batch or semi-continuous processes, which are not very suitable for industrial use. In addition, the short reaction times allow no conclusion to be drawn regarding the useful life of the catalysts.

DE-A-196 42 770 discloses the preparation of hydrogen peroxide using palladium-containing catalyst monoliths, for example V4a nets or woven fabrics impregnated with palladium. $C_1$–$C_3$-alcohols, or mixtures with water, are used as the solvent. Palladium is predominantly used as the catalytically active component; suitable promoter substances are preferably noble metals, such as platinum, rhodium, gold and silver.

None of those processes has gained acceptance for conventional $H_2O_2$ installations because of the low $H_2O_2$ concentration and, in some cases, the presence of solvents.

Not a single process has hitherto been known for the preparation of propylene oxide from propylene and hydrogen peroxide, in which hydrogen peroxide solutions which have not been concentrated and have been only crudely pre-purified are used and are returned to the hydrogen peroxide preparation again after the propylene oxidation.

Surprisingly, the Applicants have found that hydrogen peroxide solutions which have not been concentrated and have been only crudely purified can be used directly from the preparation for preparing epoxidised olefins, especially propene oxide, by the catalysed epoxidation of olefins by means of $H_2O_2$ in the presence of a zeolite, containing synthetic titanium atoms, of the general formula $xTiO_2 \cdot (1-x)SiO_2$, wherein x is in the range of from 0.0001 to 0.04.

The aqueous or aqueous-alcoholic hydrogen peroxide solutions prepared in the first stage can, after slight purification, be reacted selectively with olefins in the presence of the said zeolites containing synthetic titanium atoms to form the epoxidised olefin. The process provides for the separation and return of solvents, so that they can be returned to the hydrogen peroxide preparation process again without additional purification.

Figure 1:
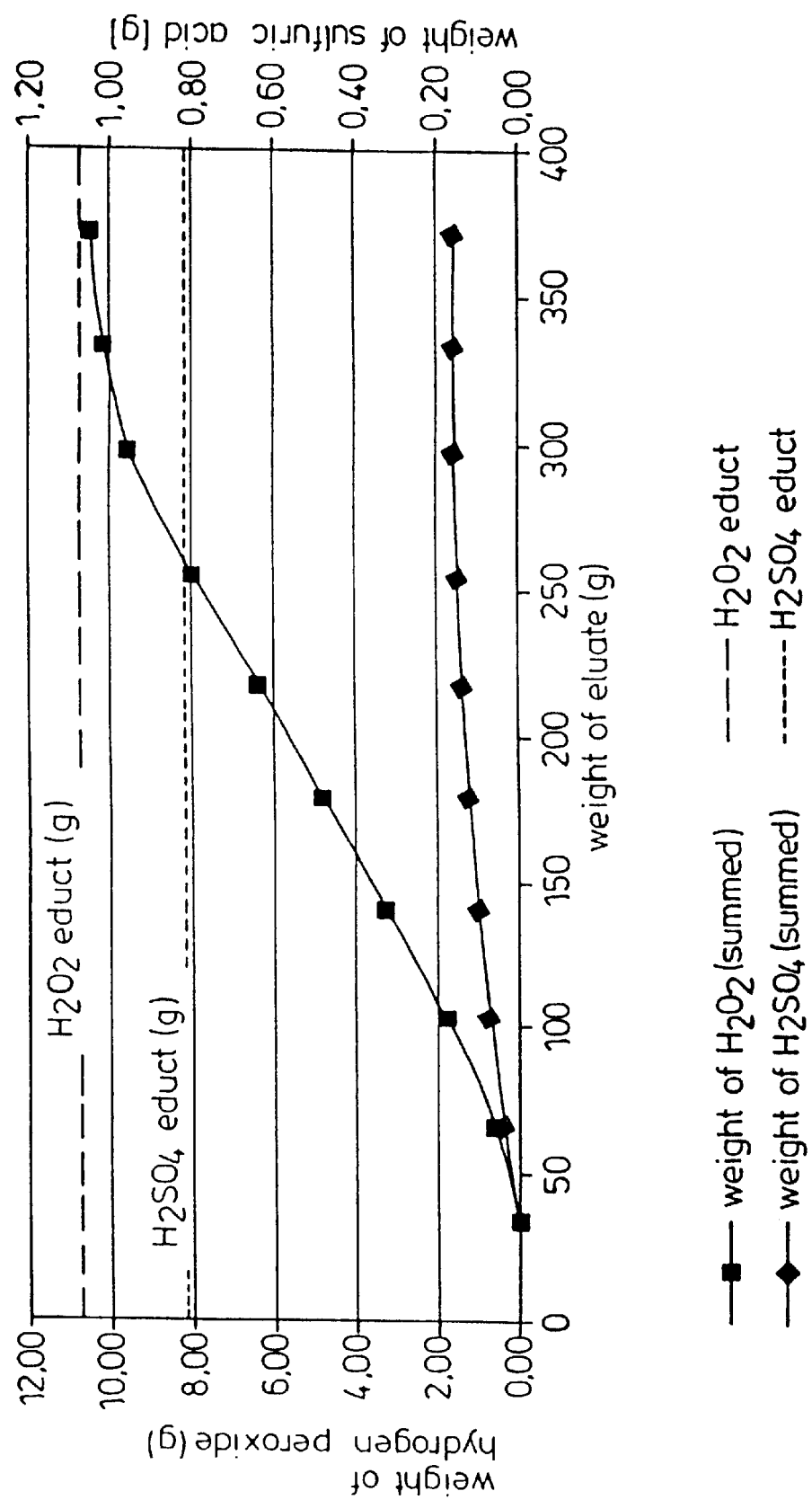
FIG. 1 is a graphic illustration of the rate of consumption of the reactants employed in the preparation of propene oxide in accordance with Example 2c).

Accordingly, the present invention relates to a process for the preparation of epoxidised olefins from olefins and alcoholic or aqueous-alcoholic dilute hydrogen peroxide solutions in the presence of a zeolite, containing synthetic titanium atoms, of the general formula $xTiO_2 \cdot (1-x)SiO_2$, wherein x is in the range of from 0.0001 to 0.04, characterised in that the process comprises the steps a) preparing the alcoholic or aqueous-alcoholic dilute hydrogen peroxide solutions by the continuous reaction of hydrogen and oxygen using catalysts that contain as the active component predominantly elements of sub-group 8, wherein those solutions may optionally additionally contain stabilisers, b) optionally inactivating the stabiliser, c) reacting the olefin with the said alcoholic or aqueous-alcoholic dilute hydrogen peroxide solution, d) separating off the epoxidised olefin, e) optionally freeing the stabiliser in the said alcoholic or aqueous-alcoholic dilute hydrogen peroxide solution, f) returning the said alcoholic or aqueous-alcoholic dilute hydrogen peroxide solution to the preparation process a), wherein the said alcoholic or aqueous-alcoholic dilute hydrogen peroxide solution is not isolated between the individual subsidiary steps.

The process according to the invention can be applied to all olefins. Preference is given to unsaturated hydrocarbons in the range of from one to twelve carbon atoms, especially ethylene, propylene, 1-butene, 2-butene, butadiene, pentenes, hexenes, isoprene, octenes and cyclohexenes.

The alcoholic or aqueous-alcoholic dilute hydrogen peroxide solutions usually have an $H_2O_2$ content in the range of from 0.5 to 15 wt. %, especially from 2 to 7 wt. %.

There are suitable as the reaction medium during preparation of the hydrogen peroxide alcohols or water or mixtures thereof.

Suitable alcohols are all alcohols known to the person skilled in the art, such as methanol, ethanol, propanol, isopropanol, butanol, pentanol, hexanol, heptanol and octanol. Of course, those alcohols may also be in branched form, such as isobutanol, sec-butanol and tert-butanol. Methanol is used as the preferred alcohol. The water may, of course, also be demineralised or distilled. The hydrogen peroxide synthesis is preferably carried out with a flooded reactor.

Suitable catalysts are all catalysts known to the person skilled in the art for the continuous reaction of hydrogen and oxygen to form hydrogen peroxide. Preference is given to catalysts that contain as the active component predominantly elements of sub-group 8, especially palladium. The catalysts are preferably used in the form of catalyst shaped bodies. Catalyst shaped bodies are catalysts in which the active catalyst component is located on the surface of supports, in particular specially shaped supports, such as Raschig rings, Sattei bodies, wire spirals or wire-mesh rings. Further examples will be found in Römpp-Chemie-Lexikon, 9th edition, page 1453 ff. Preference is also given to the use of catalyst monoliths. Catalyst monoliths are generally produced from woven fabrics, knitted fabrics, films, expanded metals and/or sheet metals. Also suitable are open-cell foams, such as polyurethane, ceramic or melamine resin foams. The active catalyst component is applied to those catalyst monoliths. The catalysts optionally contain additives of other metals, such as platinum, rhodium, iridium, copper, silver and/or gold, in order to increase the catalytic activity. The ratio of palladium to additive is in the range of from 100 to 1 to 1 to 10, especially from 10 to 1 to 1 to 1. The content of palladium and additives is generally in the range of from $5 \cdot 10^{-4}$ to 1 wt. %, especially from $10^{-3}$ to 0.15 wt. %. For further details, reference is made to DE-196 42 770, which discloses a preferred process for the preparation of alcoholic or aqueous-alcoholic dilute hydrogen peroxide solutions.

The processes described in DE-026 15 625, DE-26 55 920; U.S. Pat. Nos. 4,279,883, 4,661 337, 4,336,239, 4,379, 778; 4,389,390, EP-117 306, U.S. Pat. Nos. 4,889,705, 4,681,751, 4,772,458, 4,240,933, 4,832,938, WO-/92/04 277, U.S.Pat. No. 5,169,618, EP-579 109, EP-623 552 and WO-96/0538 are, however, also suitable.

The alcoholic or aqueous-alcoholic dilute hydrogen peroxide solutions usually contain stabilisers, which prevent the hydrogen peroxide that is formed from decomposing. The stabilisers are usually mineral acids, such as hydrochloric acid, sulfuric acid, phosphoric acid, with hydrochloric acid and sulfuric acid being preferred. They are usually used in amounts in the range of from $10^{-4}$ to $10^{-1}$ mol/l, preferably from 5 to $25 \cdot 10^{-3}$ mol/l.

Other stabilisers may optionally be present, such as those in U.S. Pat. Nos. 4,889,705 and 4,681,751. Especially advantageous are salts such as alkali bromides, alkali chlorides, alkali phosphates and alkali sulfates, more especially sodium chloride, sodium bromide, potassium chloride and potassium bromide. They are usually employed in amounts in the range of from 0.5 to 10 mmol/l, preferably from 0.5 to 2 mmol/l.

Although the added amounts of acids prove to be advantageous for stabilising hydrogen peroxide, they lead to drastic reductions in selectivity in respect of the epoxidised olefin in the epoxidation carried out in the second stage. In the presence of acids and water, the epoxides that are formed hydrolyse to the corresponding glycols and oligomeric ethers. For that reason, the acid concentration and the bromide ion concentration must be kept very low (acid content <0.5 wt. %).

In the integrated process according to the invention, the dilute hydrogen peroxide solutions are therefore advantageously rendered pH-neutral, weakly acid or weakly basic before the reaction with olefin. A pH value in the range of from 4 to 9, especially from 5 to 8, more especially from 5.5 to 7.5, is preferred. That is preferably achieved by means of a suitable ion exchanger, but other methods known to the person skilled in the art for neutralising the dilute hydrogen peroxide solutions are also suitable.

Suitable ion exchangers consist, for example, of crosslinked polymers. These support materials can be used in a wide variety of ways in heterogeneously catalysed organic reactions. Their flexibility for structural and functional changes allows the fixing of virtually all catalytically active components. Strongly acid polymers, for example those functionalised with sulfonic acid groups, can often replace mineral acids in catalytic reactions. Those acid polymers can be reversibly converted into the neutralised alkali form by means of bases. Also suitable are the ion exchangers described in Ullmann's Encyclopedia of Industrial Chemistry, 5th edition, (1989), A 14, p. 393–411.

It was surprising that fixed propene oxide selectivities of >85% are achieved if the dilute hydrogen peroxide solutions containing mineral acids are neutralised partially or completely in the described manner by means of cation exchangers before the reaction with olefin.

The reaction of the olefin with the said alcoholic or aqueous-alcoholic dilute hydrogen peroxide solution preferably takes place by the process described in EP-A1-100 119. In that process, epoxidised olefins are obtained from olefins and alcoholic or aqueous-alcoholic dilute hydrogen peroxide solutions in the presence of a zeolite, containing synthetic titanium atoms, of the general formula $xTiO_2 \cdot (1-x)SiO_2$, wherein x is in the range of from 0.0001 to 0.04. It is advantageous to improve this process by the special embodiments of EP-A1-200 260, EP-A1-230 949, DE-A1-196 23 608 and DE-A1-196 23 611, which are mentioned particularly here. Of course, it is, however, also possible to use in the integrated process according to the invention other processes for the preparation of epoxidised olefins from olefins and alcoholic or aqueous-alcoholic dilute hydrogen peroxide solutions in the presence of a zeolite, containing synthetic titanium atoms, of the general formula $xTiO_2 \cdot (1-x)SiO_2$, wherein x is in the range of from 0.0001 to 0.04.

It may also be advantageous to replace some or all of the titanium atoms by vanadium atoms. It is also advantageous to neutralise (e.g. with alkali salts, such as sodium acetate) the acid surface sites of the zeolites, containing synthetic titanium atoms, of the general formula $xTiO_2 \cdot (1-x)SiO_2$, wherein x is in the range of from 0.0001 to 0.04.

The epoxidised olefin that is formed is separated off in the conventional manner, for example by distillation, optionally under reduced pressure.

For the formation of $H_2O_2$, the reaction medium must be as proton-rich as possible, and for the epoxidation it must be as proton-deficient as possible. For the return of the alcoholic or aqueous-alcoholic dilute hydrogen peroxide solution originally used, which now has a reduced hydrogen peroxide concentration, to the said process for the preparation of alcoholic or aqueous-alcoholic dilute hydrogen peroxide solution, it may be advantageous, after separation of propene oxide, to free the optionally inactivated or neutralised stabiliser again. That is advantageously effected by adding to or passing through the depleted hydrogen peroxide solution a corresponding ion exchanger. It is especially advantageous to regenerate the previously used cation exchanger again in that manner under optionally changed reaction parameters. Of course, additional stabiliser can also be added at that stage, or stabiliser that has been used up or lost can be replaced.

Suitable ion exchangers are organic and/or inorganic polymers which have been functionalised by, for example, sulfonic acid groups (e.g. ion exchangers from Bayer AG, D (e.g. Lewatit®, Bayer Catalyst® K 1131 or K 02431) or from Rohm and Haas, USA (e.g. Amberlist® 36 W, Amberlist® 3 WET, Duolite® ARC 9652)). Also suitable are the ion exchangers described in Ullmann's Encyclopedia of Industrial Chemistry, 5th edition, (1989), A 14, p. 393–411.

Finally, the depleted hydrogen peroxide solution is returned again to the preparation process for alcoholic or aqueous-alcoholic dilute hydrogen peroxide solution (step a)).

The epoxidised olefins which can be prepared in that manner are especially ethene oxide, propene oxide.

The epoxidised olefins which can be prepared in that manner are distinguished by a high degree of purity. The entire process is very sparing and long-lasting both ecologically and economically.

The epoxidised olefins which can be prepared in that manner can be used for all applications known to the person skilled in the art, such as the preparation of polyether polyols, glycols (lubricants and antifreeze), propene oxide derivatives, and for the sterilisation of objects in the medical field.

EXAMPLES

Example 1

Preparation of catalyst monoliths with catalyst support woven fabrics of V4A

Analogously to DE 196 42 770 A1, a cylindrical V4A monolith is produced from wavy and smooth V4A nets (material: 1.4571; mesh size: 200 μm; wire diameter: 150 μm).

The monolithic support was freed of fat by the conventional methods using solvents and was placed in 80 ml of distilled water; 5 ml of a 10% $[Pd(NH_3)_4](NO_3)_2$ solution were added and stirring was carried out at 80° C. for 24 hours. The monolith is separated from the liquid phase, washed 4 times using 100 ml of demineralised water each time, dried for 2 hours at 110° C. and then reduced under nitrogen for 2 hours at 200° C. (auto-reduction by thermal decomposition of the amine complex with formation of ammonia).

Example 2 a) Preparation of Hydrogen Peroxide

The monolithic Pd catalyst of Example 1 was installed, centred about the stirrer axis, in a 400 ml V4A stirred autoclave having a gas stirrer, temperature control by means of a heat carrier, pressure maintenance to 70 bar, and a central data acquisition system. Supply pipes for hydrogen, oxygen and the reaction medium are located in the base of the reactor. In the reactor cover there is a delivery pipe from which the liquid/gas mixture is removed continuously.

The reaction medium consisted of methanol, to which 0.3 wt. % sulfuric acid, 0.03 wt. % phosphoric acid and 5 ppm of bromide (in the form of sodium bromide) were supplied. Reaction medium flows through the reactor at a volume flow rate of 100 g/h together with a constant stream of nitrogen of 60 l/h at a constant pressure of 20 bar. At the start of the reaction, the stream of nitrogen is replaced by the same total volume flow rate of oxygen and hydrogen in a ratio by volume of 92:8.

The hydrogen peroxide concentration of the resulting methanol/water solutions was from 2 to 6 wt. % hydrogen peroxide. The solution from 2a) is used directly in Example 2b).

b) Neutralisation of the $H_2SO_4/H_3PO_4/H_2O_2$-methanolic Solution of Example 2a)

Pretreatment of the ion exchanger: 100 g of Lewatit S 100 (Bayer) are stirred in 300 g of 10% NaOH for 2 hours, then filtered and washed with a total of 1.5 litres of water in portions until the washings exhibit a neutral pH. The cation exchanger in the sodium form is stirred 3 times in 100 g of methanol each time for in each case 30 minutes in order to exchange water-methanol.

The ion exchanger so pretreated was transferred with 100 g of methanol into a chromatography column (3 cm in diameter, 30 cm long; height of the Lewatit filling 12 cm).

251 g of the $H_2SO_4/H_3PO_4/H_2O_2$-methanolic solution are passed through the pretreated ion exchanger in the course of 50 minutes and are then rinsed with 150 ml of methanol, and the eluate is collected in 10 fractions each of approximately 50 ml. The acid content and the $H_2O_2$ content in the educt and in the fractions are determined by titrimetry. The hydrogen peroxide leaves the chromatography column complete, i.e. without decomposition. The sulfuric acid and phosphoric acid contained therein can be neutralised to approximately from 75 to 85% by passing once through the column (FIG. 1).

Acid titration: approximately 10 g of sample are weighed out, made up to approximately 150 ml with water and, after the addition of 5 drops of 1% phenolphthalein solution, titrated against 0.1 n NaOH (0.4 g/l) (blank value <1 drop).

$H_2O_2$ titration: 60 ml of sulfuric acid (1 mol/l) are added to 1 g of sample; the mixture is made up to 170 ml with water and titrated against 0.1 n $KMnO_4$ (3.16 g/l) (blank value <1 drop). The solution of Example 2b) is used directly in Example 2c).

c) Preparation of Propene Oxide

In a 1 litre stirred autoclave having a magnetic stirrer, temperature control by means of water, a thermocouple, and supply pipes in the base of the reactor for the freshly prepared partially neutralised hydrogen peroxide solution from 2b) (approximately from 3 to 5%) and for gaseous propylene. In a typical preparation method, 500 g of the dilute hydrogen peroxide solution are placed at 45° C. in the reactor flushed with nitrogen, 2 g of synthetic titanium silicalite having titanium contents of 2.8 wt. % are suspended as described in EP-A1-100 119, and gaseous propylene is metered in, with vigorous stirring, to a pressure of 4 bar. Further propylene is metered in as it reacts; the pressure of 4 bar therefore remains constant. Under those conditions, the epoxidation to propene oxide takes place very quickly and selectively. After 70 minutes, more than 95% of the hydrogen peroxide has been used up and a propene oxide selectivity of from 85 to 92% is found (FIG. 1).

d) Freeing of the Stabiliser from 2b)

After the removal of propene oxide by distillation, the depleted solution from 2c) was passed through the chromatography column used in 2b) in the opposite direction.

The neutralised acid was converted into the acid form again to the extent of over 70 to 80%. The pH value was <1.

What is claimed is:

1. A process for the production of an epoxidized olefin comprising
   a) preparing a dilute hydrogen peroxide alcoholic or aqueous-alcoholic solution by continuous reaction of hydrogen and oxygen in the presence of (i) a catalyst containing a metal of sub-group 8 of the Periodic Table of Elements as its active ingredient and (ii) a stabilizer,
   b) inactivating the stabilizer with an ion exchanger,
   c) reacting an olefin with the dilute hydrogen peroxide solution in the presence of a zeolite catalyst containing synthetic titanium atoms represented by the formula $$xTiO_2 \cdot (1-x) SiO_2$$

in which x represents a number of from 0.0001 to 0.04,
   d) recovering epoxidized olefin formed during the reaction of b) from the reaction mixture, and
   e) returning the dilute hydrogen peroxide solution remaining after recovery of the epoxidized olefin to preparation step a)
   in which dilute hydrogen peroxide solution is not isolated until after the epoxidized olefin has been recovered.

2. A process for the production of an epoxidized olefin comprising
   a) preparing a dilute hydrogen peroxide alcoholic or aqueous-alcoholic solution by continuous reaction of hydrogen and oxygen in the presence of (i) a catalyst containing a metal sub-group 8 of the Periodic Table of Elements as its active ingredient and (ii) a stabilizer,
   b) recovering the stabilizer with an ion exchanger,
   c) reacting an olefin with the dilute hydrogen peroxide solution in the presence of a zeolite catalyst containing synthetic titanium atoms represented by the formula $$xTiO_2 \cdot (1-x)SiO_2$$

in which x represents a number of from 0.0001 to 0.04,
   d) recovering epoxidized olefin formed during the reaction of c) from the reaction mixture, and
   e) returning the dilute hydrogen peroxide solution remaining after recovery of the epoxidized olefin to preparation step a) in which dilute hydrogen peroxide solution is not isolated until after the epoxidized olefin has been recovered.

3. A process for the production of an epoxidized olefin comprising
   a) preparing a dilute hydrogen peroxide alcoholic or aqueous-alcoholic solution by continuous reaction of hydrogen and oxygen in the presence of (i) a catalyst containing a metal of sub-group 8 of the Periodic Table of Elements as its active ingredient and (ii) a stabilizer,
   b) reacting an olefin with the dilute hydrogen peroxide solution in the presence of a zeolite catalyst containing synthetic titanium atoms represented by the formula $$xTiO_2 \cdot (1-x) SiO_2$$

in which x represents a number of from 0.0001 to 0.04,
   c) recovering epoxidized olefin formed during the reaction of b) from the reaction mixture,
   d) inactivating the stabilizer with an ion exchanger, and
   e) returning the dilute hydrogen peroxide solution remaining after recovery of the epoxidized olefin to preparation step a) in which dilute hydrogen peroxide solution in not isolated until the epoxidized olefin has been recovered.

4. The process of claim 1 in which the stabilizer is a mineral acid.

5. The process of claim 1 in which the catalyst employed in step a) includes palladium or a palladium-metal mixture.

6. The process of claim 1 in which propylene is used as the olefin.

7. An epoxidized olefin produced by the process of claim 1.

8. An epoxidized olefin produced by the process of claim 2.

9. An epoxidized olefin produced by the process of claim 3.

10. An epoxidized olefin produced by the process of claim 6.

11. A process for the production of a polyether polyol comprising reacting the epoxidized olefin produced by the process of claim 6 with a suitable starter material.

* * * * *